(12) United States Patent
Kuniavsky et al.

(10) Patent No.: US 10,349,834 B2
(45) Date of Patent: *Jul. 16, 2019

(54) SENSING HEALTH USING FLUID SENSORS IN FEMININE HYGIENE PRODUCTS

(71) Applicant: Palo Alto Research Center Incorporated, Palo Alto, CA (US)

(72) Inventors: Michael Kuniavsky, San Francsico, CA (US); Siqi Wang, Emeryville, CA (US)

(73) Assignee: PALO ALTO RESEARCH CENTER INCORPORATED, Palo Alto, CA (US)

(*) Notice: Subject to any disclaimer, the term of this patent is extended or adjusted under 35 U.S.C. 154(b) by 141 days.

This patent is subject to a terminal disclaimer.

(21) Appl. No.: 15/395,829

(22) Filed: Dec. 30, 2016

(65) Prior Publication Data

US 2018/0184904 A1 Jul. 5, 2018

(51) Int. Cl.
| A61F 13/84 | (2006.01) |
| A61B 5/145 | (2006.01) |
| A61B 5/00 | (2006.01) |
| A61B 5/1455 | (2006.01) |
| A61F 13/15 | (2006.01) |
| A61B 5/022 | (2006.01) |

(52) U.S. Cl.
CPC .......... *A61B 5/0022* (2013.01); *A61B 5/0008* (2013.01); *A61B 5/14532* (2013.01); *A61B 5/14539* (2013.01); *A61B 5/14546* (2013.01); *A61B 5/14551* (2013.01)

(58) Field of Classification Search
CPC .......... A61B 13/84; A61F 13/42; A61F 13/15; A61B 5/022; A61B 5/0015; A61B 5/0002; A61B 5/14532; A61B 5/145; A61B 5/14539; A61B 5/14546; A61B 5/14555

USPC ......................................... 422/82.01; 436/151
See application file for complete search history.

(56) References Cited

U.S. PATENT DOCUMENTS

| 5,079,174 | A * | 1/1992 | Buck ................ G01N 33/54386 422/408 |
| 7,344,499 | B1 * | 3/2008 | Prausnitz .......... A61M 37/0015 600/309 |
| 8,053,625 | B2 * | 11/2011 | Nhan ....................... A61F 13/42 604/361 |
| 8,911,988 | B2 * | 12/2014 | Miller .................. A61B 5/1405 435/288.7 |
| 8,933,292 | B2 * | 1/2015 | Abraham ................ A61F 13/42 604/361 |
| 9,907,707 | B2 * | 3/2018 | LaVon ..................... A61F 13/42 |
| 2010/0148183 | A1 * | 6/2010 | Ward ...................... B82Y 20/00 257/76 |

FOREIGN PATENT DOCUMENTS

| CA | 2921637 A1 * | 8/2016 | ............. A61F 13/84 |
| WO | WO 2010/049829 A2 * | 5/2010 | ............. A61F 13/42 |

* cited by examiner

*Primary Examiner* — Christine T Mui
(74) *Attorney, Agent, or Firm* — Shun Yao; Park, Vaughan, Fleming & Dowler LLP

(57) ABSTRACT

One embodiment of the present invention provides an apparatus for analyzing substances within a liquid. The apparatus includes an absorber that comprises one or more layers of absorbent material for absorbing the liquid and one or more sensors embedded within the one or more layers of absorbent material. The sensors are configured to provide information associated with the substances included in the absorbed liquid. The apparatus further includes electrical conductive traces coupled to the one or more sensors, thereby facilitating transmission of outputs of the sensors.

20 Claims, 13 Drawing Sheets

SENSING HEALTH USING FLUID SENSORS IN FEMININE HYGIENE PRODUCTS

BACKGROUND

Field

The present disclosure relates to personal health monitoring. More specifically, the present disclosure relates to feminine hygiene products with built-in heath-monitors.

Related Art

The rapid development of mobile computing technologies has opened the door for wearable health monitoring devices, including devices that can monitor a user's body temperature, heart rate, sleeping pattern, blood pressure, etc. Although having the advantage of being portable and non-invasive, most of these wearable health-monitoring devices can only provide limited information about a person's health.

SUMMARY

One embodiment of the present invention provides an apparatus for analyzing substances within a liquid. The apparatus includes an absorber that comprises one or more layers of absorbent material for absorbing the liquid and one or more sensors embedded within the one or more layers of absorbent material. The sensors are configured to provide information associated with the substances included in the absorbed liquid. The apparatus further includes electrical conductive traces coupled to the one or more sensors, thereby facilitating transmission of outputs of the sensors.

In a variation on this embodiment, the absorber is part of: a disposable feminine hygiene product (FHP), a disposable diaper, or a disposable wound dressing.

In a variation on this embodiment, the sensors include one or more of: a capacitance sensor, a conductance sensor, a chemical sensor, and a biological sensor.

In a further embodiment, the biological sensor include a printable carbon-nanotube based sensor.

In a variation on this embodiment, the liquid comprises body fluid.

In a further variation, the substances include one or more of: a biological substance and a chemical substance.

In a variation on this embodiment, the apparatus further includes one or more of: a microprocessor coupled to the sensors via the electrical conductive traces, a near-field communication (NFC) tag, and a radio-frequency identification (RFID) tag.

One embodiment provides an apparatus for analyzing a liquid contained in an absorbent material. The apparatus includes a needle array for penetrating the absorbent material to extract the liquid and one or more sensors coupled to the needle array. The sensors are configured to provide information associated with substances included in the liquid. The apparatus further includes electrical conductive traces coupled to the one or more sensors, thereby facilitating transmission of outputs of the sensors.

One embodiment provides a feminine hygiene product (FHP). The FHP includes an absorber that comprises one or more layers of absorbent material for absorbing menstrual fluid and one or more sensors embedded within the one or more layers of absorbent material. The sensors are configured to provide information associated with the substances included in the menstrual fluid. The FHP further includes electrical conductive traces coupled to the one or more sensors, thereby facilitating transmission of outputs of the sensors.

One embodiment provides a system for obtaining health information associated with a user of a feminine hygiene product (FHP). During operation, the system receives outputs from one or more sensors embedded in an absorption layer of the FHP, which absorbs the user's menstrual fluid. The system analyzes the outputs of the sensors to obtain information associated with one or more biological or chemical substances included in the menstrual fluid and extracts health information associated with the user based on levels of the biological or chemical substances.

BRIEF DESCRIPTION OF THE FIGURES

In the figures, like reference numerals refer to the same figure elements.

DETAILED DESCRIPTION

Overview

Figure 1A:
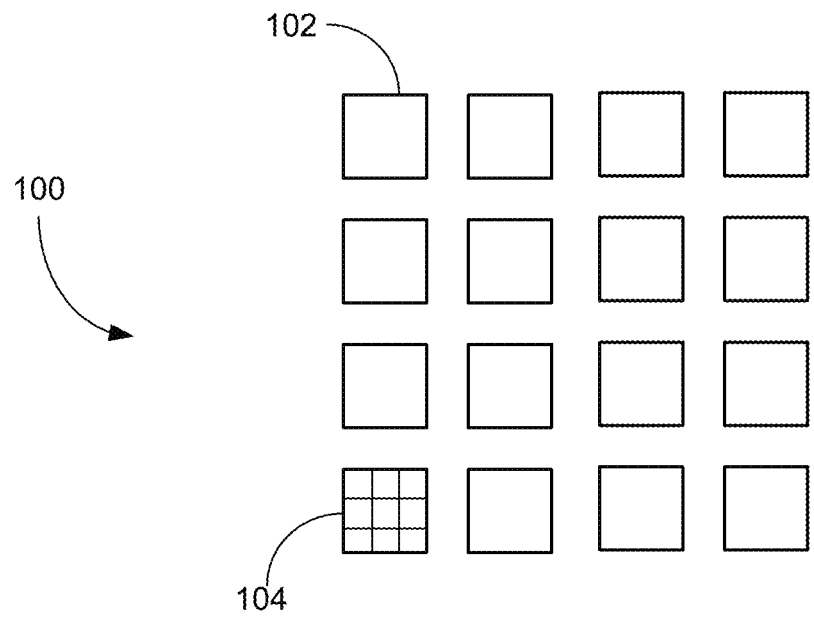
FIGS. 1A and 1B present diagrams illustrating exemplary sensor groups, in accordance with an embodiment of the present invention.

Embodiments of the present invention provide a "smart" feminine hygiene product (FHP) (e.g., tampons, sanitary pads, pantyliners, menstrual cups, etc.) that can provide information associated with the health of its user. More specifically, the smart FHP can include one or more embedded sensors that can be in contact with menses collected by the FHP. The one or more sensors can sense various physical, chemical, and biological properties of the menses, thus providing various types of information related to the health of the user. In some embodiments, the status of the sensors can be reported to the user using visual effects. In some embodiments, printable circuitry can also be used to couple the sensors to processing unit that can analyze the sensor data and output the sensor data using a user-readable format.

FHP with Embedded Sensors

While there are many wearable devices on the market that can provide useful health-related information to users, none of the devices is specifically designed to address the various health issues that uniquely affect women. Many gynecologic disorders or diseases can be asymptomatic, and patients may not know their existence until it is too late. On the other hand, even after some women notice pain or discomfort, they may attribute such pain or discomfort to the natural menstrual cycle and, hence, ignore it.

Although regular screening at a doctor's office or hospital can provide timely detections of gynecologic disorders or diseases, the screening process can be painful or invasive and often costly. In certain parts of the world, many women may consider seeing a gynecologist an embarrassment and often skip necessary preventive care. Women need special, discreet tools that can allow them to monitor their own health on a regular basis at a low cost.

Smart FHP technology takes advantage of the fact that, during menstruation, menstrual fluid can be discharged from a women's body, and that for hygiene purposes, most women use certain types of FHPs to collect the menstrual fluid. Because the menstrual fluid can include material that was part of the women's body, such as blood, cervical mucus, vaginal secretions, and endometrial tissue, one can extract information associated with the women's health by testing the menstrual fluid. More specifically, the smart FHP technology can be implemented by incorporating sensors into the FHP, either by embedding into the absorbent material or by printing onto the surfaces.

Because most women have regular menstrual cycles, using a smart FHP to obtain information associated with a women's health can make it possible for the woman to have constant surveillance of her personal health without the need to perform any other sample-collecting operation. For example, using the smart FHP, a woman can have a daily blood test for a week every month without using any intrusive (e.g., finger poking) method. In addition, because the menstrual fluid contains other types of body material in addition to blood, a smart FHP can also provide health information that may not be available from a blood test.

Various types of sensors can be used to provide health information. For example, a simple capacitance sensor can be used for sensing fluid volume. Because the volume, frequency, and pattern of the menstruation can be related to women's health, volume measurements correlated with time (e.g., by incorporating the capacitance sensor with a timer) can provide useful information related to women's health. Moreover, the volume sensor may also indicate to the user that the FHP is at its capacity, and to prevent leakage, the user may want to change to a new one. Conductance sensors can be used to detect the presence of the fluid, together with its salinity and composition.

In some embodiments, multiple sensors can be grouped together to measure the presence and concentration of multiple substances. In further embodiments, a particular sensor for measuring a particular substance may be formed using an array of sensors having the same sensing elements. For example, a carbon nanotube (CNT)-based biosensor array can be used to identify specific biogenic substances; and an array of reactive chemical sensors can also be used to measure the presence and concentration of multiple chemical substances. Both the biosensors and the chemical sensors can produce electrical signals, because they rely on changes in electrical properties (e.g., electrical resistance) to detect substances. In addition, photometric chemical sensors can also be used to detect certain chemical properties associated with the menstrual fluid, such as pH values.

FIG. 1A presents a diagram illustrating an exemplary sensor group, in accordance with an embodiment of the present invention. Sensor group 100 can include multiple sensors (e.g., sensors, 102 and 104), each being configured to detect and/or measure at least one substance, such as a biogenic substance (e.g., human hormone or virus), a chemical substance (e.g., birth control medication), and an element (e.g., oxygen, calcium, or iron). Some of the sensors in sensor group 100 (e.g., sensor 102) can be a single sensor, whereas some of the sensors in sensor group 100 (e.g., sensor 104) can include a sensor array, which can be a CNT-based biosensor array.

Figure 1B:
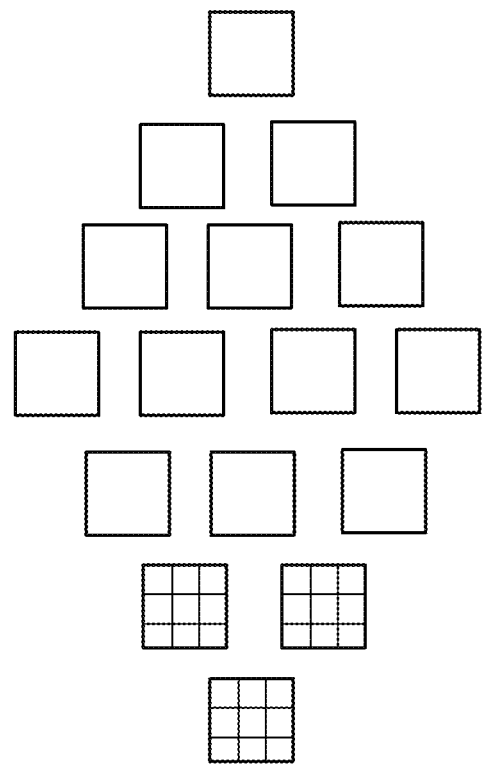

In addition to the two-dimensional array formation shown in FIG. 1A, the sensors in the sensor group can also be arranged into different types of formation, such as the one shown in FIG. 1B. The scope of this invention is not limited to the arrangement of the sensors.

Figure 2:
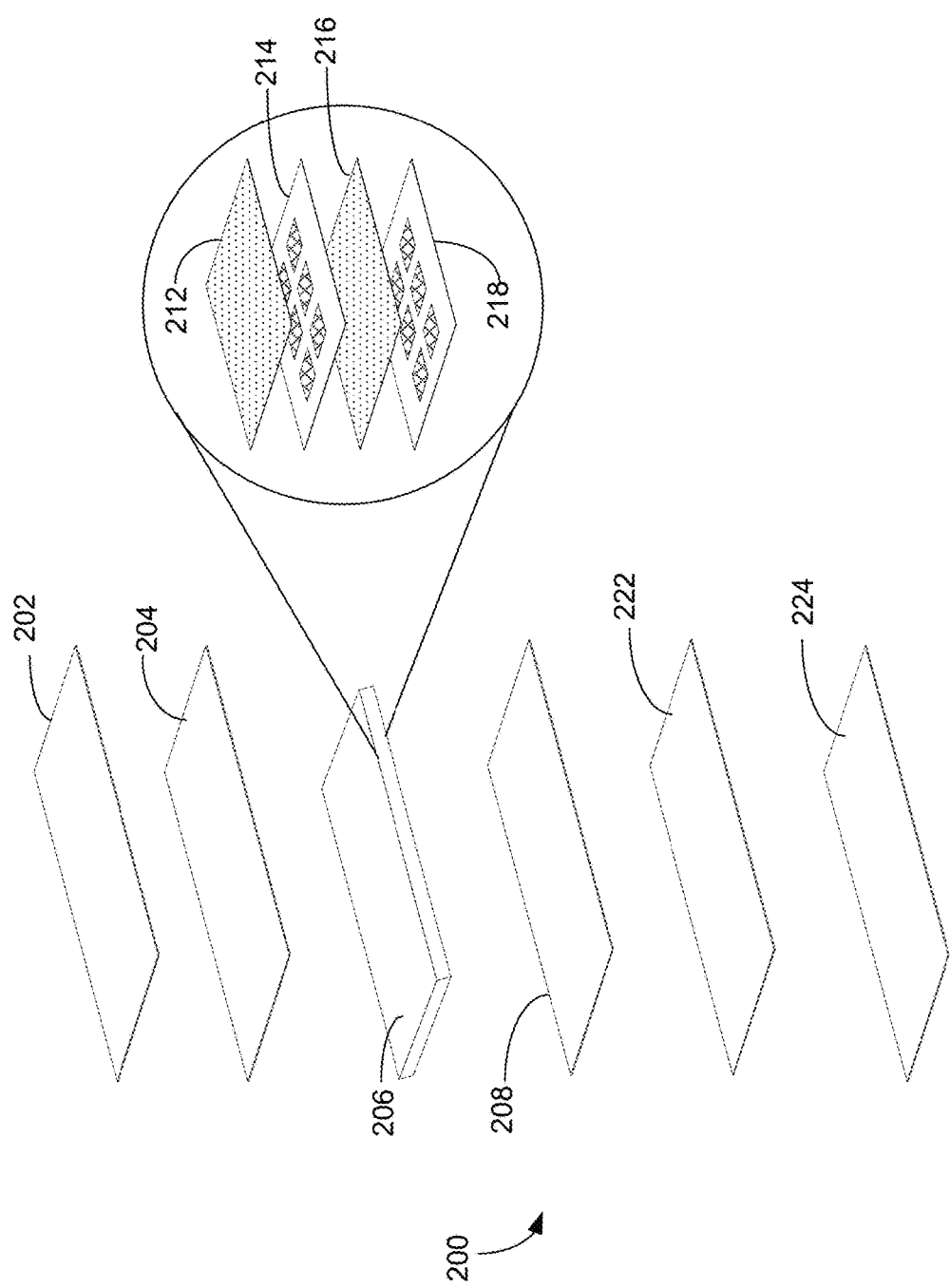
FIG. 2 presents a diagram illustrating the layered structure of an exemplary smart sanitary pad, in accordance with an embodiment of the present invention.

FIG. 2 presents a diagram illustrating the layered structure of an exemplary smart sanitary pad, in accordance with an embodiment of the present invention. Like any conventional sanitary pad or napkin, smart sanitary pad 200 can include multiple layers. More specifically, smart sanitary pad 200 can include a top sheet 202, which can include a quick absorbing lining that can be the receiving surface of the menstrual fluid. The quick absorbing lining can include funnel-shaped pores that allow instant infiltration of fluid while preventing backflow. Because top sheet 202 can come into direct contact with the user's skin, top sheet 202 typically is made of hypoallergenic materials.

Paper layers 204 and 208 can be used to sandwich absorption layer 206. More specifically, each of the paper layers 204 and 208 can include one or more layers of dust-free paper. Absorption layer 206 is the main body of smart sanitary pad 200, and can include highly effective absorbent materials for absorbing the menstrual fluid along with embedded sensors for detecting various substances contained within the menstrual fluid. In some embodiments, absorption layer 206 itself can also include multiple layers, such as one or more layers made of absorbent agents and one or more layers that include sensors and connecting circuitry. In the example shown in FIG. 2, absorption layer 206 can include, from top down, a filter layer 212, a sensor layer 214, a filter layer 216, and a sensor layer 218. More specifically, filter layers 212 and 216 are made of absorbent agents that expand as they absorb the menstrual fluid. Note that, because different substances may be absorbed at different rates by the absorbent agents, filter layers 212 and 216 can also function as chromatographic tools that separate the different substances, with certain substances being tested by sensors on sensor layer 214, while other substances tested by sensors on sensor layer 218. For effective separation of the substances, in further embodiments, filter layers 212 and 216 may include different materials or have different packing densities. Layout of sensors on sensor layers 214 and 218 can be arranged based on the properties (e.g., speed of diffusion) of the substances.

Sensor layers 214 and 218 can include not only the various sensors but also the circuitry that may connect the sensors to a processing chip (e.g., a Si-based processing chip). The processing chip can process information detected by the sensors and can report the processed information to an external device. Alternatively, the processing chip may not have the computational capacity for processing information detected by the sensors. Instead, the processing chip may simply report the sensor status to an external device, which then records and processes such information. For example, the processing chip may interface with an application running on a smartphone of the user, reporting the sensor status to the smartphone app, which can then process the sensor status to extract information related to the user's health. In some embodiments, the processing chip can include a near-field communication (NFC) or radio-frequency identification (RFID) tag. In addition to NFC and RFID, other wireless communication mechanisms can also be used to transmit the sensor data, including but not limited to: Bluetooth and infrared. The connecting circuitry can be printed on the same flexible substrate on which the sensors were grown, if the sensors are CNT-based sensors. For example, hybrid printed electronics technology can be used to achieve a sensing-and-transmitting system that uses printable electronics (which can include printable sensors, multiplexers, conductive traces, antennas, and ancillary passive elements) alongside Si-based microelectronic devices used for analog-to-digital conversion, processing, and wireless transmission.

In the example shown in FIG. 2, the sensors and absorbent agents are shown on different layers. In practice, they may have different formations, and different methods can be used to embed the sensors. For example, instead of having a layered structure, absorption layer 206 may include a continuous body of absorbent agents, and the sensors along with the connecting and/or processing circuitry can be embedded inside the continuous body of absorbent agents. Alternatively, the sensors and the connecting circuitry may have a 3D structure and can be woven between absorbent fibers of the sanitary pad.

Smart sanitary pad 200 can also include a backsheet 222, which can be permeable to air but not water, and an adhesive base layer 224.

In addition to sanitary pads or napkins, the same technology can be used in other types of FHP, such as tampons, pantyliners, menstrual cups, etc. Depending on the type of the FHP, different methods may be needed to embed the sensors. For example, because the absorption layer included in pantyliners is usually much thinner than the one included in a sanitary pad or napkin, and because a pantyliner is expected to collect a lesser amount of fluid, a smart pantyliner may include fewer sensors. Moreover, when used in tampons, the layout of the sensors and the connecting circuitry may need to adapt to the shape and compact size of the tampon. On the other hand, the lack of absorbent materials used on menstrual cups means that the sensors may need to be printed, directly, onto the inner surface of the menstrual cups to make contact with the menstrual fluid.

Moreover, the sensing-and-transmitting system that employs printable sensors can also be used in other products that deal with body fluids, such as diapers (baby or adult), nursing pads, wound dressings (e.g., Band-Aids or bandages), incontinence products, clothing, shoe inserts and linings, seats and beddings, etc. By embedding sensors inside the absorbent materials that absorb the body fluids during normal usage, embodiments of the present invention provide a solution for a user to obtain health-related information in a non-invasive and private manner.

Figure 3:
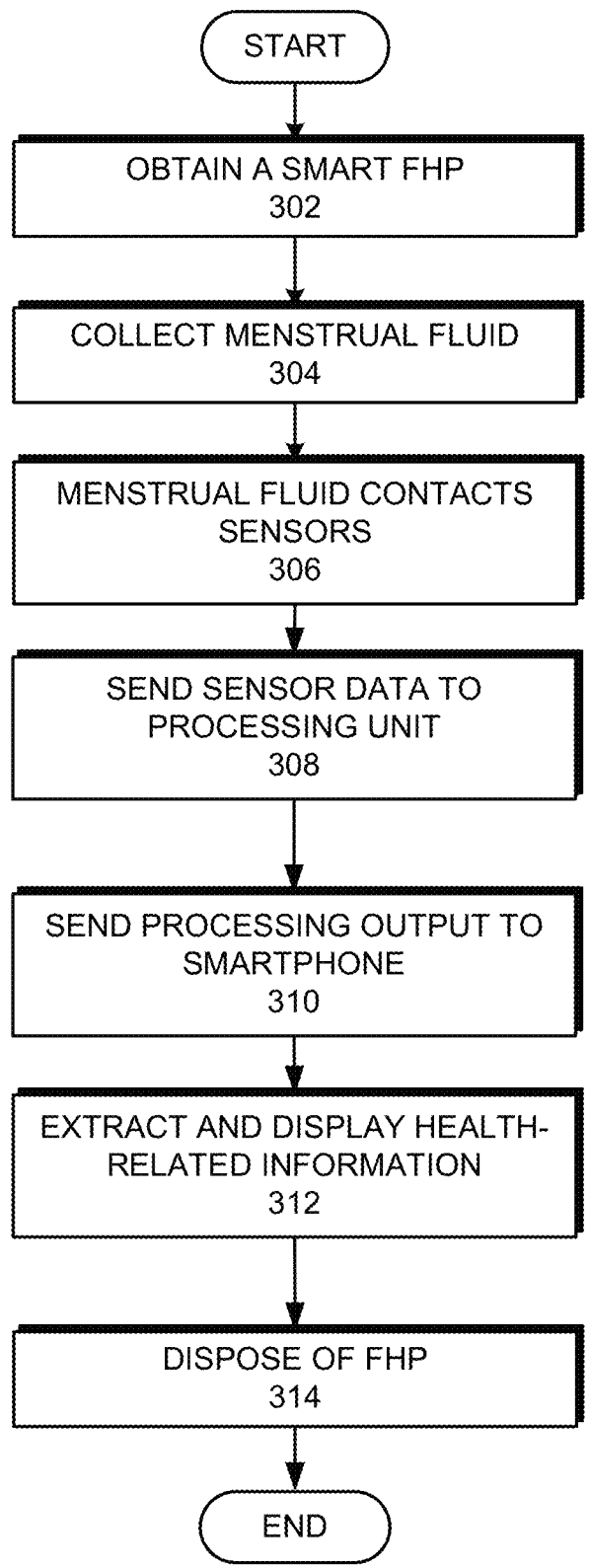
FIG. 3 presents a flowchart illustrating an exemplary use case of a smart FHP, according to an embodiment of the present invention.

FIG. 3 presents a flowchart illustrating an exemplary use case of a smart FHP, according to an embodiment of the present invention. A user can obtain a smart FHP (e.g., a sanitary pad) (operation 302). The user can use the smart FHP in a way that is similar to the usage of conventional FHPs. The smart FHP collects menstrual fluid (operation 304). The collected menstrual fluid can come into contact with various sensors incorporated into the smart FHP (operation 306). The sensors can include but are not limited to: a conductance sensor, a capacitance sensor, an array of biosensors, and a array of chemical sensors. In some embodiments, absorbent agents included in the FHP can act as chromatographic filters to spatially separate various substances included in the menstrual fluid, and the various sensors can be arranged based on the properties of the substances they intend to detect.

Subsequent to the sensors detecting the substances and/or their concentration, the sensor data can be sent to a processing unit (operation 308). The processing unit can be located on or off the FHP. In other words, the processing unit can be part of the smart FHP or can be located on an external device. The processing unit can perform simple or complex data analysis on the sensor data to obtain various types of information, including but not limited to: the current flow rate of the menstrual fluid, body temperature, level of birth-control medicines, amount of oxygen, amount of iron, pH balance, level of hydration, blood alcohol level, glucose level, lactobacilli level, existence of different viruses (e.g., HPV or HIV virus), presence of bacteria, and histamine levels. The outcome of the analysis by the processing unit can optionally be transmitted to an application running on the user's smartphone or can be uploaded to cloud-based analysis services (operation 310). The smartphone app can extract health-related information, and provide, via a user interface, the health-related information to the user (operation 312). Moreover, the smartphone app or analysis service can also maintain past health information associated with the user and, hence, can correlate the health information with time. For example, based on data obtained from different time instances, the system can identify patterns of menstruation (e.g., flow patterns). By monitoring changing levels of certain substances (e.g., pH balance, lactobacilli, etc.), the system may identify potential problems associated with the user's vaginal health. On the other hand, by monitoring levels of iron and glucose, the system may identify problems associated with the user's general health. In some embodiments, data collected from a large number of users over a relatively long time period can also be used as input to certain population-health-analysis algorithms to obtain health information associated with the population. For example, such data may be used to predict population-level trends and the progression of diseases.

After usage, the smart FHP can be disposed of in a way similar to that for disposing of a conventional FHP (operation 314).

Handheld Sensing Device

In addition to embedding sensors or sensor arrays inside a disposable product (e.g., FHP), in some embodiments, the sensors or sensor arrays may be placed inside a separate handheld device that can collect and test samples from absorbent materials. For example, a user may place the handheld device on top of a soiled FHP, and the handheld device can collect and test the menstrual fluid absorbed by the FHP.

In some embodiments, the handheld device can include an array of needles or microneedles that can penetrate absorbent material (e.g., absorbent agents in an FHP), and capillary action can result in the fluid contained inside the absorbent material flowing into the needle tubes and encountering sensors inside the needle tubes. In some embodiments, a single needle may include a single sensor for detecting a particular chemical or biological substance. In some embodiments, a single needle may include a sensor array (e.g., a CNT-based biosensor array) for detecting one or multiple substances. In some embodiments, multiple needles and their included sensors may be grouped together to form a sensor array. In addition to the needle array, the handheld device can include an extended handle that allows a user to hold the handle while performing the testing, thus reducing the chances of the user's hand touching the soiled absorbent material.

The handheld device can also include electronic circuitry and, optionally, a processing unit for outputting and processing the sensor data. In some embodiments, the processing unit can receive raw data from each sensor and perform necessary processing to analyze the content of the body fluid under test. For example, the processing unit may obtain measurements of substances within the menstrual or other types of body fluid contained in the absorbent material. In some embodiments, the handheld device may simply transmit raw sensor data to a separate computing device, which can be local to the user or in a remote data processing center. The separate computing device can then perform computations based on the received raw sensor data in order to extract health-related information.

In some embodiments, the result and/or analysis of the sensor data can be sent to an application running on the user's smartphone or other mobile devices. The user can then get a report regarding her health by opening the user interface of the application.

Figure 4A:
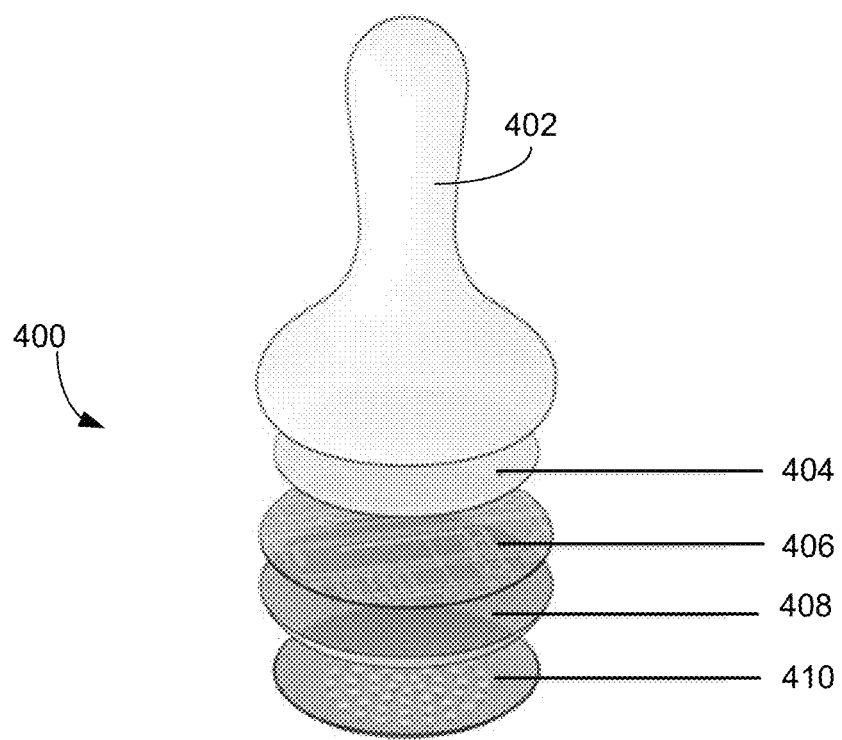
FIG. 4A illustrates the exploded view of an exemplary handheld body-fluid-testing device, in accordance with an embodiment of the present invention.

FIG. 4A illustrates the exploded view of an exemplary handheld body-fluid-testing device, in accordance with an embodiment of the present invention. In FIG. 4A, a handheld body-fluid-testing device 400 includes a handle 402, a microprocessor 404, a sensor layer 406, a battery layer 408, and a needle array 410.

Figure 4B:
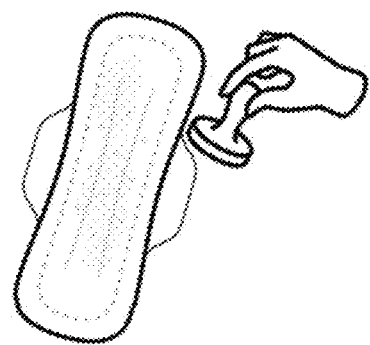
FIG. 4B illustrates an exemplary scenario of operating a handheld body-fluid-testing device, in accordance with an embodiment of the present invention.

Handle 402 can allow the user's hand to be kept at the minimum distance to the sample under test, thus reducing the chances for contamination. FIG. 4B illustrates an exemplary scenario of operating the handheld body-fluid-testing device 400, in accordance with an embodiment of the present invention. In FIG. 4B, a user is holding the handheld body-fluid-testing device by its handle, and can press the detecting surface of the handheld body-fluid-testing device onto a soiled sanitary pad to collect and test menstrual fluid absorbed by the sanitary pad.

Returning to FIG. 4A, microprocessor 404 can be responsible for processing the data collected by the multiple sensors located on sensor layer 406. In some embodiments, microprocessor 404 can also be coupled to a wireless communication module, which can transmit the sensor data as well as the processing results to an external device. The sensors on sensor layer 406 can be coupled to the needles in needle array 410. In some embodiments, sensor layer 406 includes sensor circuitry, whereas the sensing elements (e.g., elements that react with the to-be-detected substances) are attached to the needles in needle array 410. The types of sensors included in sensor layer 406 can be similar to the ones embedded into the FHP, as shown in FIGS. 1A-1B and FIG. 2.

Battery layer 408 can provide a battery for powering both the sensors and microprocessor 404. Moreover, battery layer 408 can include mechanisms for coupling the sensors and the needles in needle array 410. Note that FIG. 4A is for illustration purposes only and does not limit the relative locations of the various components. For example, instead of being positioned between sensor layer 406 and needle array 410, the battery may be placed at other locations, as long as it can be electrically coupled to the sensors and microprocessor 404.

Needle array 410 can include an array of needles or microneedles that can penetrate absorbent materials to collect liquid samples. In some embodiments, handheld device 400 is reusable while needle array 410 can be disposable. In other words, after each use, the user may discard the sample-collecting needles and, optionally, the sensors attached to the needles, while keeping all other components for future use. It is also possible for the user to reuse these needles. However, after each use, the needles need to be sterilized to prevent cross-contamination.

In addition to needle array 410, in some embodiments, the sensing surface of handheld body-fluid-testing device 400 can also have other types of sample-collecting means. For example, pad sensors can be installed on the sensing surface that can detect substances upon contacting the surface of the absorbent materials. Alternatively, optical sensors can also be used to detect color changes of the absorbent materials. For example, the absorbent material may change color at certain locations corresponding to the pH values of the body fluid.

In the example shown in FIGS. 4A and 4B, the handheld body-fluid-testing device is configured like a stamp that can fit a normal hand, and a user is expected to press the stamp onto the surface of the absorbent material to extract and test liquid held by the absorbent material. In practice, the handheld body-fluid-testing device may have different shapes, sizes, or configurations. For example, the body-fluid-testing device may have a simpler form (e.g., handleless) and can be much smaller. In some embodiments, specially designed "stickers" can be used to test body fluid contained in absorbent material.

Figure 5A:
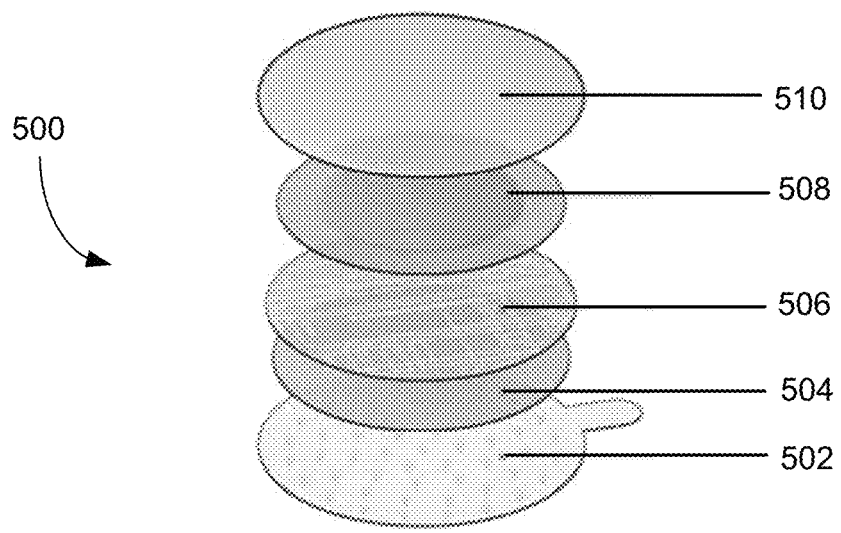
FIG. 5A illustrates the exploded view of an exemplary body-fluid-testing sticker, in accordance with an embodiment of the present invention.

Like the handheld body-fluid-testing device, the specially designed testing stickers can have a needle array or microneedle array for extracting fluid from absorbent materials. The needle or microneedle array can facilitate the testing stickers to be stuck onto the surface of the absorbent materials (e.g., the surface of a sanitary pad). The testing stickers can further include sensors and, optionally, a processing unit or microprocessor. FIG. 5A illustrates the exploded view of an exemplary body-fluid-testing sticker, in accordance with an embodiment of the present invention.

In FIG. 5A, a body-fluid-testing sticker 500 includes a needle array 502, a battery layer 504, a sensor layer 506, a microprocessor 508, and a top sheet 510. Needle array 502 can be similar to needle array 410 shown in FIG. 4A. All the other layers can also be similar to the corresponding layers shown in FIG. 4A. However, due to its size limit, sensor layer 506 may have fewer sensors than sensor layer 406 shown in FIG. 4A. In some embodiments, instead of having different types of sensors, sensor layer 506 may only include a single sensor or a sensor array configured to detect a particular substance within or a particular property of the body fluid. For example, a pH-testing sticker can be used to measure the pH value of the body fluid, or a glucose-testing sticker can be used to measure the glucose level. Other types of sensors can also be used in each individual testing-sticker to allow the user to test for different substances or properties. In some embodiments, multiple stickers can be used simultaneously to provide the user with multiple pieces of health-related information.

Figure 5B:
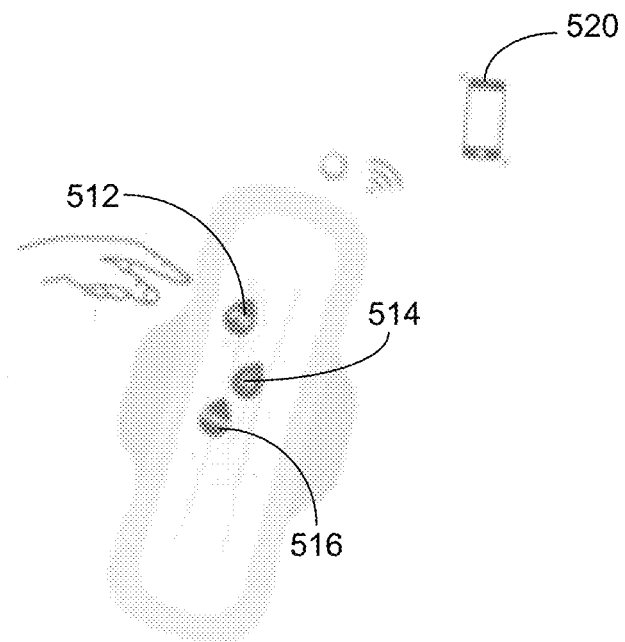
FIG. 5B illustrates an exemplary scenario of applying multiple testing stickers, in accordance with an embodiment of the present invention.

FIG. 5B illustrates an exemplary scenario of applying multiple testing stickers, in accordance with an embodiment of the present invention. In FIG. 5B, multiple testing stickers (e.g., a sticker 512 for testing the pH value, a sticker 514 for testing the hydrogen level, and a sticker 516 for testing the level of a particular human hormone) can be simultaneously applied onto a soiled sanitary pad, each configured to detect a particular type of substance and transmit the sensor data to a smartphone 520. After usage, the stickers can be discarded along with the soiled sanitary pad.

In some embodiments, testing stickers can be attached to the package that holds the FHPs such that the consumer can purchase the FHP along with the testing stickers. For example, each individually packaged sanitary pad may include in its package one or more testing stickers. Alternatively, the testing stickers can be sold separately, and a consumer can choose which type of testing stickers to purchase based on her need for certain health-related data. For example, if a user is particularly concerned with monitoring for a yeast infection, she may choose a testing sticker that can measure and correlate the volume of vaginal *lactobacillus* with the volume of menstrual fluid, which is a good indicator of a potential occurrence of yeast infection. Alternatively, if the user is more concerned with diabetes, she may choose a testing sticker that can test the blood glucose level.

Containers with Built-in Sensors

In addition to embedding the sensors into the absorbent material or using needles to extract liquid from the absorbent material, in some embodiments, the body-fluid-containing absorbent material can also be tested while it is placed inside a waterproof package or container. More specifically, sensors or sensor arrays can be attached (either by direct printing or by other attachment mechanisms) to the inner surface of the waterproof package or container. When absorbent material containing to-be-tested liquid is placed inside the package or container, the sensors or sensor arrays can come into contact with the to-be-tested liquid to detect and measure certain types of substances included in the liquid. The sensor status can be transmitted to external devices for processing.

After testing, the "smart" package and the to-be-tested material can be discarded together. This can allow hygienic and discreet testing of many different kinds of liquid-containing objects, including but not limited to: FHPs, baby or adult diapers, nursing pads, wound dressings, cleaning products, etc. The smart package can also be used to hold crime scene evidence, which can sometimes include fabric or other materials soaked with blood. Other types of biological or chemical samples can also be analyzed using the smart package instead of being handled directly by users. More specifically, placing the samples (e.g., soiled diapers or FHPs) inside the package often requires minimum user handling. Unlike traditional testing, the user of the smart package is not required to collect liquid from the samples, which can be a daunting task for amateurs.

In some embodiments, the sensors may be placed in such a way that a user may need to drop the to-be-tested sample in a particular orientation to ensure contact between the sensors and liquid contained in the sample. For example, if the sensors are printed on one side of the package, the user may need to drop the sample with the liquid-containing surface facing the sensor side of the package. In some embodiments, the sensors may be placed in such a way that they can test samples that are randomly placed inside the container. For example, sensors can be printed on both sides of the package, and regardless of its orientation, the liquid-containing surface can be exposed to the sensors.

Figure 6A:
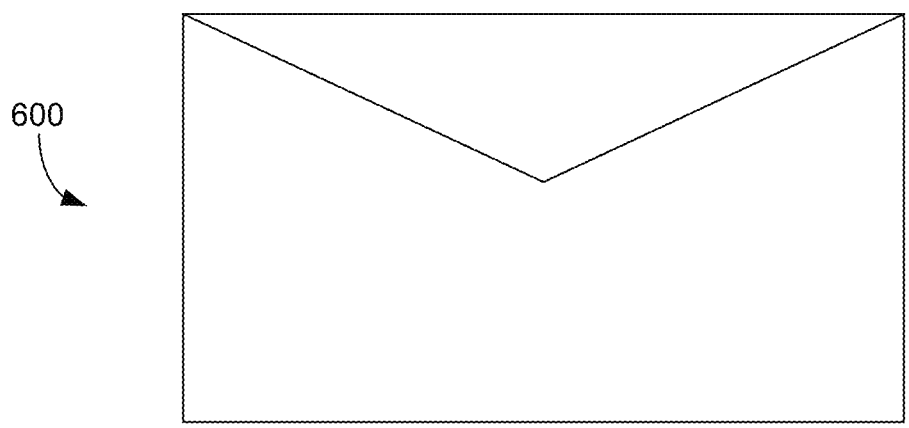
FIG. 6A illustrates an exemplary smart package, in accordance with an embodiment of the present invention.
Figure 6B:
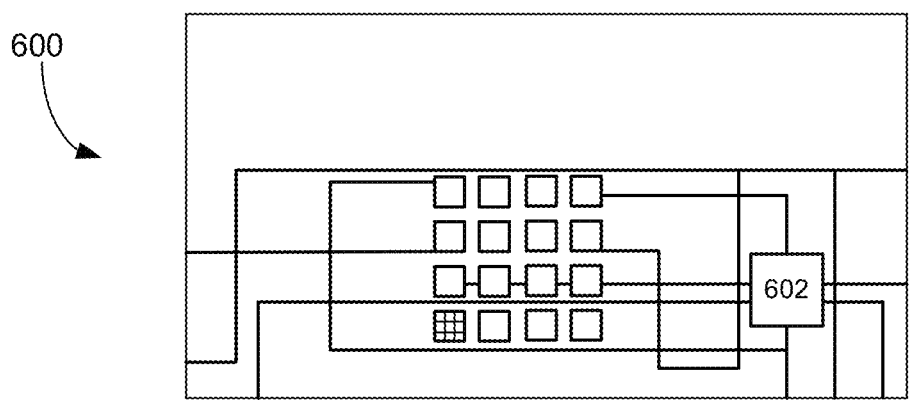
FIG. 6B shows an inner surface of the smart package, in accordance with an embodiment of the present invention.

FIG. 6A illustrates an exemplary smart package, in accordance with an embodiment of the present invention. FIG. 6B shows an inner surface of the smart package, in accordance with an embodiment of the present invention. When viewed from the outside, smart package 600 can look like a conventional envelope. Although it is possible to use paper, to prevent leakage, smart package 600 can be made of waterproof materials, such as plastics or biaxially oriented polyethylene terephthalate (BoPET). Smart package 600 can also have multiple layers, the inner layer being waterproof.

In FIG. 6B, multiple sensors, including sensor arrays, can be printed onto at least one of the inner surfaces of smart package 600. In addition to the printable sensors, other printable components, such as conductive traces and ancillary passive elements, can also be printed onto the inner surface of smart package 600. In some embodiments, smart package 600 can also include a processing and communication unit 602, which can process the sensor data and transmit the sensor data and analysis result to an external device.

Figure 6C:
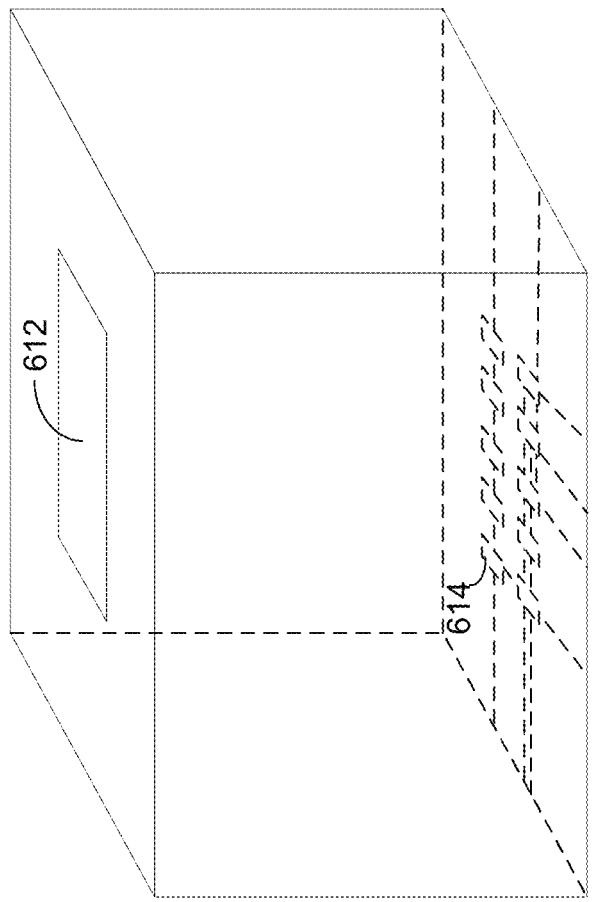
FIG. 6C illustrates an exemplary smart container, in accordance with an embodiment of the present invention

FIG. 6C illustrates an exemplary smart container, in accordance with an embodiment of the present invention. Smart container 610 can include a physical enclosure shaped like a rectangular prism having an opening 612. A number of sensors (e.g., sensor 614) can be printed onto the inner bottom surface of container 610. When a sample containing biological or chemical substances is dropped inside container 610 from opening 612, the sensors can detect the biological or chemical substances. In some embodiments, the sensor data can be processed by a processor attached to smart container 610, and processing results can be displayed by a display attached to smart container 610. Other than the rectangular prism, smart container 610 can have different shapes.

Figure 7:
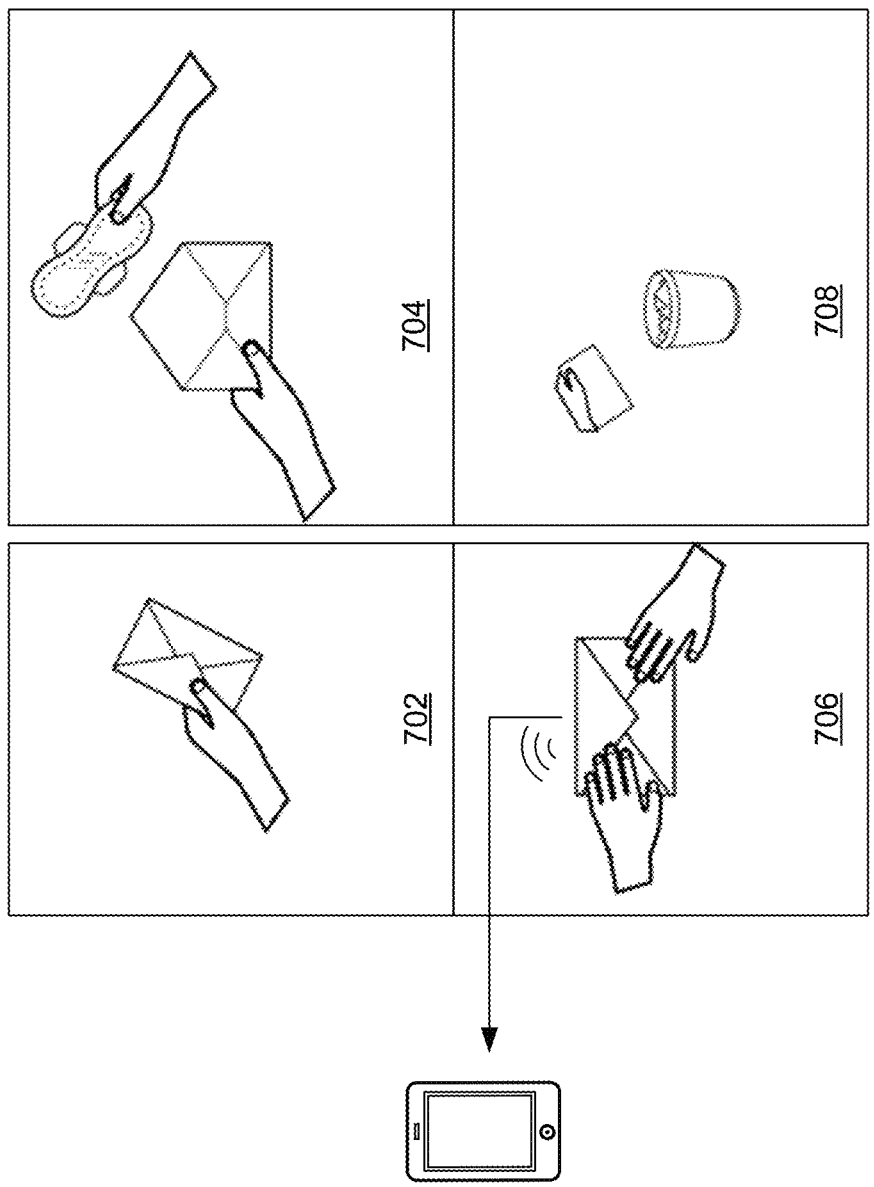
FIG. 7 illustrates an exemplary use scenario of the smart package, in accordance with an embodiment of the present invention.

FIG. 7 illustrates an exemplary use scenario of the smart package, in accordance with an embodiment of the present invention. In operation 702, a user may obtain a smart package. Depending on the dimensions of the sample, the smart package may have various shapes and sizes. In this example, the smart package can be an envelope suitable for testing sanitary pads. In operation 704, the user places a soiled sanitary pad inside the envelope. Depending on the design (e.g., the way sensors were printed on the inner surface of the envelope), the user may need to arrange the sanitary pad so that the soiled surface will face the sensors. It is also possible for the sensors to be printed on all of the inner surfaces of the envelope so the user may randomly drop in the to-be-tested item.

In operation 706, the user seals the envelope. For flexible packages (e.g., the envelope), the user may press the package against its contents to ensure sufficient contact between the to-be-tested sample and the sensors. Because the package is waterproof and has been sealed, doing so will not cause leakage or contamination. The sensors located on the inner surface of the package can then sense the various substances within the menstrual fluid contained in the soiled sanitary pad. The raw or processed sensor data can then be transmitted to an external device (e.g., the user's smartphone), which can perform health analysis and display the results to the user.

In operation 708, the user discards the sealed envelope along with its contents. If the envelope contains forensic evidence or industrial samples, the envelope may be stored for future use.

As one can see from FIG. 7, the smart package provides a hygienic and discreet way for a user to perform at-home testing of body fluids. There are other advantages to using the smart package for sample storage and testing. A sealed package can prevent or minimize contamination of the to-be-tested sample. This can be important in many scientific, forensic, or industrial usages. In some embodiments, depending on the usage, the smart package can also be pre-treated with certain chemicals or include desiccants to preserve the samples. The sealed package also allows discreet transport of the samples. Other people will not know the contents of the package. The package itself can also protect the people handling hazardous samples. For example, certain forensic evidence may have sharp edges (e.g., broken glasses, or knives); placing such evidence inside a sealed package for testing can prevent injury.

In the example shown in FIG. 7, the sensor data or testing results are sent wirelessly to an external device. In practice, different methods can be used to obtain the sensor data. In some embodiments, the sensor circuitry can extend from the inner surface of the package to the outer surface such that an external reader can be electrically coupled to the sensors in order to read the sensor data. In some embodiments, the smart package may include photometric chemical sensors containing fluorescent dyes, and the sensor results can be read optically from the exterior of the package. In some embodiments, the exterior of the smart package may include a display (e.g., an E-Ink display), which can be printed on or embedded in the outer surface of the package. Metadata associated with the content of the package, including the sensor data, can be displayed.

In addition to flexible materials, such as paper and plastics, the smart package can also be made of non-flexible materials, such as glass or metal. In some embodiments, in addition to printed sensors, the smart package or container itself can include non-electric sensing materials, such as color-changing materials, that can be used to sense certain substances. For example, a smart package can be made by laminating a layer of color-changing material (e.g., litmus paper) on the inside of a transparent protective outer layer. The package itself may change color in response to the property of or substances within the contents of the package.

In addition to the rectangular shape shown in FIG. 7, the smart package can have many different shapes and sizes. In some embodiments, the dimensions of the smart package or container can be designed based on its intended uses. Other than the envelope or container shown in FIGS. 6A-7, the smart package can take on other formats, such as a pouch, a bag, or any other devices that includes a partially or fully enclosed space for holding a sample.

Moreover, in addition to sensors for detecting liquid material, the smart package or container may also include gas sensors that can detect gaseous substances released by the item sealed in the container. For example, a smart diaper pail may be installed with print-on gas sensors that can monitor and analyze gases released by the dirty diapers and remind the user to empty the pail or alert the user to certain health conditions related to the baby.

Removable Testing Strip and External Tester

In aforementioned embodiments, different methods were used to test liquid (e.g., body fluid) contained in absorbent materials, including embedding sensors into the absorbent material, using a handheld device to extract and test the liquid, and placing the absorbent material into a smart package having printed sensors. Implementations of hybrid printed electronics technology have made it possible to integrate the printable sensors with Si-based components (e.g., processors or wireless transmitters). However, including the Si-based components can add cost and can be bulky.

In some embodiments of the present invention, absorbent material containing body fluid may include a smaller removable portion embedded with sensors, and an external reader can be used to interface with removable portion to extract the sensor data. For example, a sanitary pad can include, within its absorption layer, a small removable section that is formed by perforating the absorbent material, adding a non-permeable support layer and a tab extending out of the back surface of the sanitary pad. The tab allows the user to remove the cut-out section from the backside of the sanitary pad. This can minimize contact between the user's fingers and the soiled side of the sanitary pad. The location and size of the removable section can be carefully designed to ensure that a sufficient amount of the sample (e.g., menstrual fluid) can be collected for analysis.

After removing the removable section from the larger sample (e.g., a soiled sanitary pad or a dirty diaper), a user can place the removable section onto a specially designed reader to extract sensor data. In some embodiments, the specially designed reader may also include, on its surface, sensors that can perform additional sensing functions. In some embodiments, the removable section may not include embedded sensors and the external reader does all the sensing.

Figure 8A:
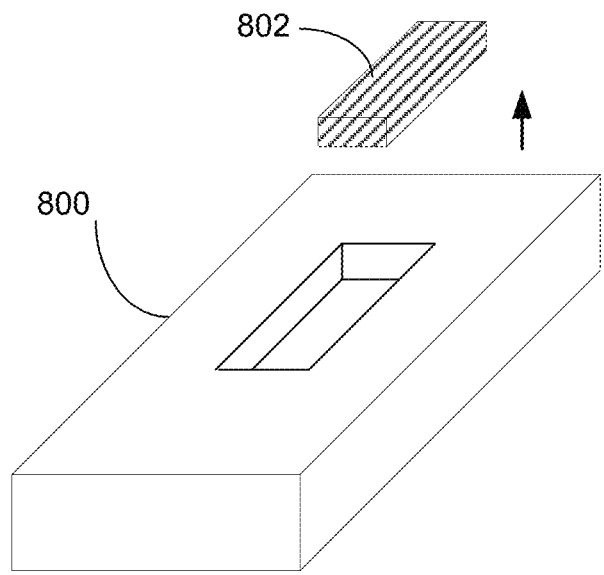
FIG. 8A illustrates an exemplary absorber with a removable body-liquid testing strip, in accordance with an embodiment of the present invention.

FIG. 8A illustrates an exemplary absorber with a removable body-liquid testing strip, in accordance with an embodiment of the present invention. More specifically, absorber 800 can be part of a personal hygiene product (e.g., an FHP or diaper) or a medical product (e.g., a wound dressing), which absorbs body fluid, and can be made of any suitable material. Absorber 800 can include a removable testing strip 802. When absorber 800 is in use, testing strip 802 can be embedded inside absorber 800, absorbing body fluid. In some embodiments, testing strip 802 can include a number of sensors or sensor arrays. The embedded sensor or sensor arrays can be similar to the ones shown in FIGS. 1A-1B. Subsequent to using the personal hygiene product, a user can lift up testing strip 802, as shown in FIG. 8A. To minimize the user's physical contact with the body fluid, absorber 800 can be configured in such a way that testing strip 802 is lifted up from the backside (i.e., the side opposite to the soiled surface) of the personal hygiene or medical product. In addition to diapers and FHPs, absorber 800 can also be used in other products that may absorb fluid, such as cleaning products.

In some embodiments, testing strip 802 can optionally be reinforced using a sheet of material that facilitates its removal from absorber 800. For example, testing strip 802 can be attached (e.g., glued) to a plastic tab, and a user can remove testing strip 802 by pulling the plastic tab. At least a portion of the plastic tab is separated from the absorbent material by a layer of non-permeable material to allow the user to pull the tab without touching the absorbent material. In additional to plastic, other types of material, such as fabric, metal, glass, etc., can also be used to reinforce testing strip 802, as long as the reinforcing material is stiffer than the absorbent material in absorber 800. In some embodiments, absorber 800 and testing strip 802 can be designed in such a way that the removal of testing strip 802 can result in another non-absorbent or non-permeable component being extracted to fill or cover the void left by testing strip 802. For example, as the user is pulling away or lifting up testing strip 802, another sheet of plastic can be pulled from the back surface of absorber 800, covering the void.

Figure 8B:
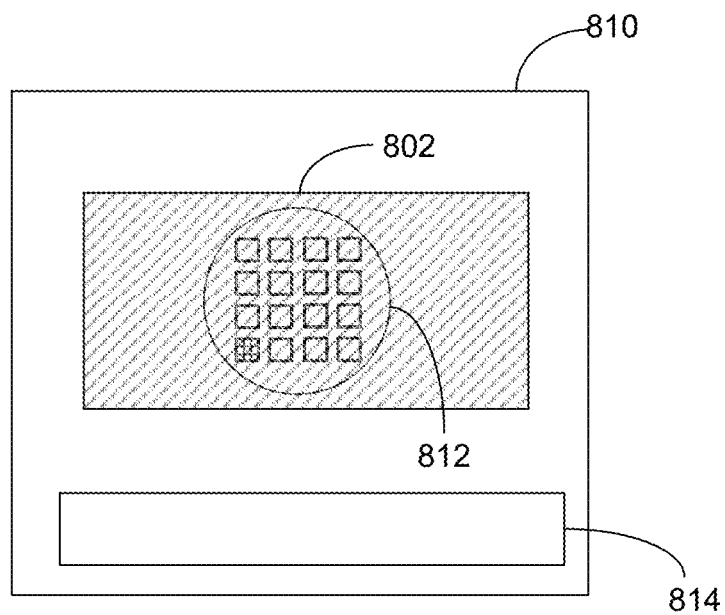
FIG. 8B illustrates an exemplary external testing device, in accordance with an embodiment of the present invention.

Testing strip 802 can then be placed onto an external testing device 810, as shown in FIG. 8B. External testing device 810 can include readers capable of reading sensor data from sensors embedded in testing strip 802. For example, testing strip 802 may include an RFID tag coupled to the sensors, and external testing device 810 may include an RFID reader. In the example shown in FIG. 8B, external testing device 810 also includes a sensor region 812 with embedded sensors or sensor arrays. This way, even if testing strip 802 does not contain embedded sensors, by having direct physical contact with testing strip 802, the sensors in sensor region 812 can sense the various substances included in the body fluid. In some embodiments, external testing device 810 can include a display 814 that can display the extracted sensor data or health analysis results.

Figure 9:
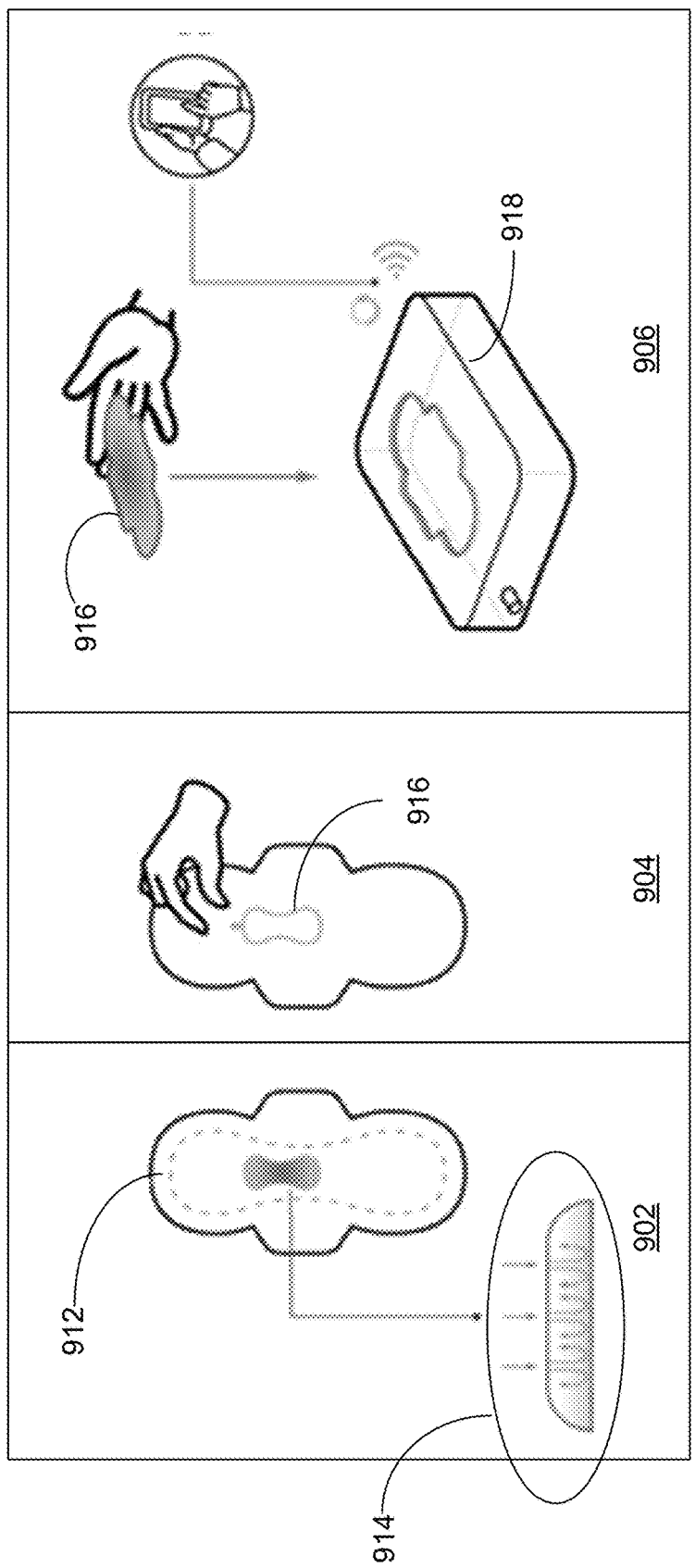
FIG. 9 illustrates an exemplary use scenario of the removable testing strip and external tester, in accordance with an embodiment of the present invention.

FIG. 9 illustrates an exemplary use scenario of the removable testing strip and external tester, in accordance with an embodiment of the present invention. In operation 902, a user is using a sanitary pad 912 having a removable testing strip to collect menstrual fluid. The usage of the sanitary pad can be the same as the usage of any conventional sanitary pad. Like conventional sanitary pads, sanitary pad 912 includes absorbent material that only allows liquid to permeate in one direction (as illustrated by drawing insert 914). Absorbed fluid will not flow back even after pressing.

In operation 904, the user can lift up, from the backside of sanitary pad 912, removable or peel-able testing strip 916. Removable testing strip 916 can include a tab for easy peeling. Because the tab is on the backside of sanitary pad 912, it usually is not contaminated by the menstrual fluid. After removing testing strip 916, the user can discard the sanitary pad as usual.

In operation 906, the user can place testing strip 916 on external tester 918. In some embodiments, external tester 918 can include a void that holds testing strip 916. In some embodiments, external tester 918 can have a flat surface. As discussed earlier, external tester 918 can also include sensors and a display. External tester 918 can transmit the extracted sensor data and, optionally, analysis results to an app running on the user's smartphone.

In the examples shown in FIGS. 8A-8B and FIG. 9, there is only one removable section. In practice, the absorber may include multiple removable sections, each used for testing a different substance. This can be useful when the absorbent material acts as a chromatographic filter and different substances have been spatially separated.

Incorporating removable testing strips into the absorbers of the various hygiene products can provide a number of advantages. Sample storage can become much simpler. Instead of storing bulky items, such as diapers or pads, the user only needs to store a small testing strip, which can be placed into a small sterile package for later use. Furthermore, it is easier to keep the process of storing or testing smaller samples hygienic and discreet.

In some embodiments, the product can include a visual indication that shows the user the location of the removable testing strip. For example, the removable testing strip can have a different color or can be marked by a border. This tells the user which part of the absorber will be used for sensing.

To ensure that sufficient amount of sample can be obtained, the user may wish to place the product a certain way. For example, when applying wound dressings, a user may wish to place the removable testing strip closer to the center of the wound.

The removal of the testing strip can indicate to users that a testing sample has been collected from a product. In some embodiments, special designs can be used to enhance the visual effect. For example, the absorbent material underneath the testing strip can be dyed a different color. This way, a user can clearly see the void left by the removed testing strip.

Chromatography-Aided Substance Sensing

As discussed previously, the absorbent material contained in personal hygiene or medical products (e.g., diapers, sanitary pads, nursing pads, bandages, paper towels, etc.) can sometimes act as a chromatographic filter, because the different substances contained in the absorbed liquid (e.g., blood or urine) diffuse differently in the absorbent material. For example, plasma and leukocytes in blood can have different diffusion speeds in absorbent materials. This property can be useful for detecting the various substances contained in the absorbed liquid. More specifically, the absorbent material can act as the stationary phase in chromatography to spatially separate the various substances. Various known chromatography techniques and materials can be used.

The spatial separation of substances can be used to aid the identification of the substances. In some embodiments, the sensing results may be displayed using visual effects. For example, by pre-calibrating the absorbent material, one can know the range of separation of the different substances. Accordingly, different parts of the absorbent material in a product can be impregnated with different chemically color-changing materials, which can be arranged in patterns based on the expected diffusion of the absorbed liquid.

Figure 10B:
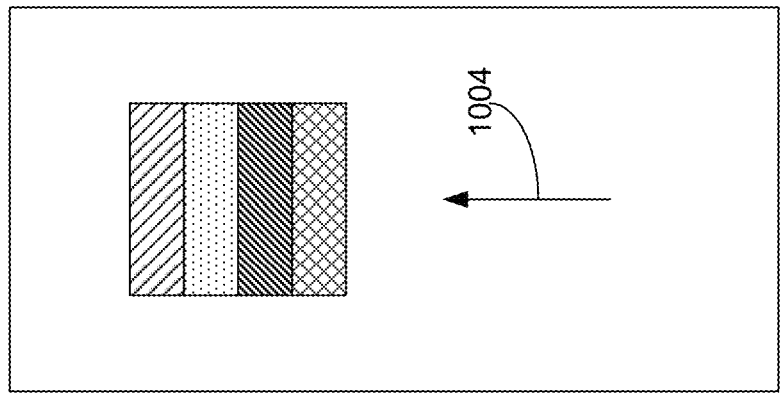
FIGS. 10A and 10B illustrate exemplary absorbers embedded with chromatographic indicators, in accordance with an embodiment of the present invention.
Figure 10A:
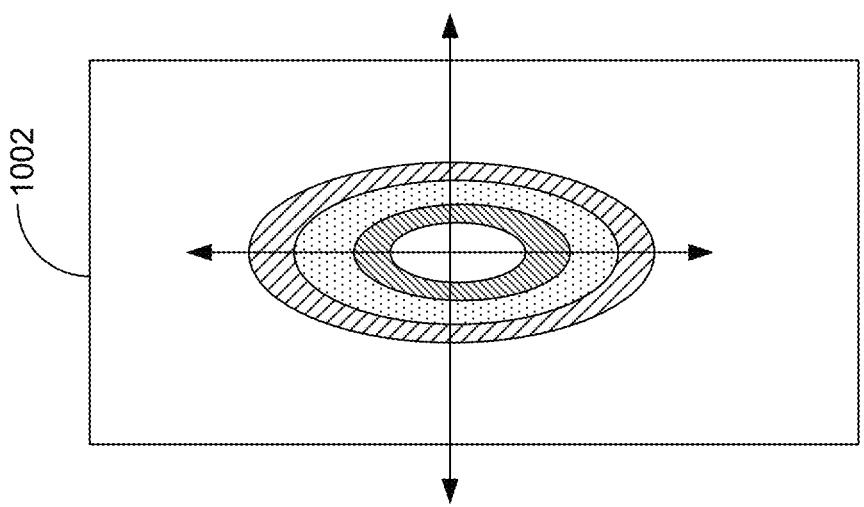

FIG. 10A illustrates an exemplary absorber embedded with chromatographic indicators, in accordance with an embodiment of the present invention. In FIG. 10A, the surface of an absorber 1002 can be include a printed pattern of various chemically color-changing materials. More specifically, the printed pattern can include a number of concentric rings, with each individual zone containing a particular chemically color-changing material. In other words, different zones can react to different substances (e.g., chemical or biological substances) and can change to different colors. This way, as the various substances diffuse as predicted, a particular substance can react with a particular color-changing material. Each zone becomes an individual sensor that senses an individual substance. Because the diffusion properties of the substances result in a particular substance having a higher concentration at a particular zone, each zone can then be more likely to produce a higher quality result than the scenario where the absorbed liquid was treated as a uniform body.

In the example shown in FIG. 10A, the absorbed liquid diffused concentrically, as indicated by the arrows. This can be the case of a sanitary pad or nursing pad. In some cases, the absorbed liquid may diffuse, at least partially, in a certain direction, and the printed pattern of the chemically color-changing materials may be different. FIG. 10B illustrates a different scenario where absorbed liquid diffuses in a direction as indicated by arrow 1004. Accordingly, different chemically color-changing materials can form a pattern that includes multiple parallel strips. This can be the case of a diaper. At a location far away from the liquid entry point, it can be viewed that the liquid is diffusing in one direction.

The sensing results, i.e., the color-changing results, can provide direct visual indication to the user of certain substances. In some embodiments, optical sensors can also be used to read the color-changing results, and outputs of the optical sensors can be analyzed to provide health-related information.

In some embodiments, the chromatographic effect can be combined with electronic sensors to provide more effective ways to detect substances. More specifically, the spatial separation of the substances makes it possible to place sensors at corresponding locations. For example, a chemical sensor for detecting a certain chemical can be placed at the location where the chemical will have a higher concentration after diffusion.

Figure 11B:
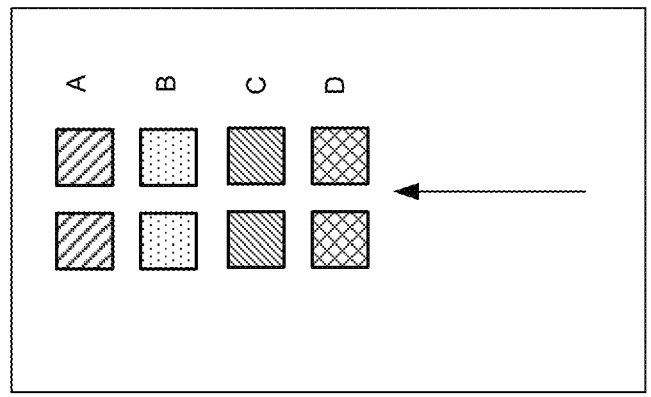
FIGS. 11A and 11B illustrate groups of sensors embedded inside absorbent material, in accordance with an embodiment of the present invention.
Figure 11A:
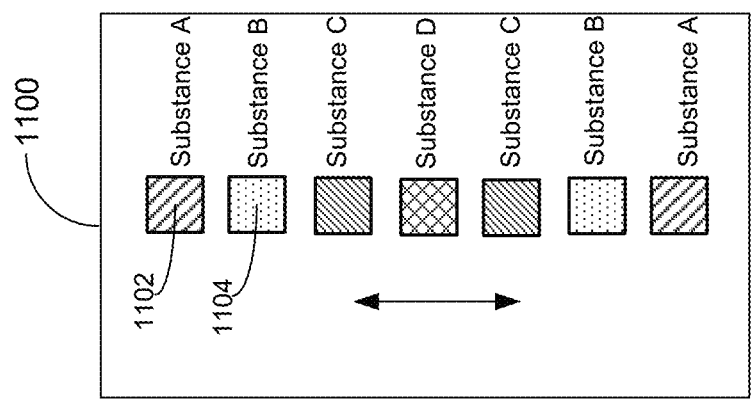

FIG. 11A shows a group of sensors embedded inside absorbent material, in accordance with an embodiment of the present invention. In FIG. 11A, a number of sensors are embedded inside absorber 1100, such as sensors 1102 and 1104. Absorber 1100 can be made of various absorbent materials, such as paper, cellulose fibers, cotton, hydrocolloid dressing, and a combination of hydrocolloid non-permeable dressing and absorbent fabric. The sensors can be similar to the sensors shown in FIGS. 1A and 1B. The different sensors can sense the presence and concentration of different substances. For example, sensor 1102 can be used for sensing substance A, whereas sensor 1104 can be used for sensing substance B. The way that the sensors are arranged is based on the diffusion property of the various substances. In the example shown in FIG. 11A, the liquid is diffusing in both directions (as indicated by the double ended arrow), and substance A diffuses the fastest. As a result, sensors for detecting substance A can be placed the furthest away from the center of diffusion. All the other sensors, the ones for sensing substances B, C, and D, are also placed based on the diffusion properties of substances B, C, and D.

In some embodiments, instead of using different sensors to detect the different substances, simple conductance or capacitance sensors can be used to detect the different diffusion speeds of the substances and, hence, the presence of the different substances.

FIG. 11B shows another scenario where the absorbed liquid diffuses in one direction, as indicated by the arrow. Similar to what shown in FIG. 11A, sensors for sensing substance A are placed further away from the starting point of the diffusion.

In addition to sensors, other electronic components, such as conductive traces, processors, and transmitters can also be embedded in the absorber, similar to what is shown in FIG. 2. If the absorber includes thin layers of paper or fabric, the sensors and conductive trances can be directly printed onto the surface of the paper or fabric, similar to the example shown in FIG. 6B.

Certain chemicals that can assist in the sensing of substances can also be placed (by infusing, embedding, printing, or injecting) at special locations (also known as chemical reaction zones) within the absorber based on diffusion properties of the substances that may react with the chemicals. For example, glucose oxidase (which is used for testing glucose levels) can be strategically placed at particular locations within the absorbent material of a sanitary pad. Biosensors for testing the glucose levels can then be embedded or printed at those locations to measure the concentration of the oxidized glucose, reflecting the blood glucose level of the user.

Similar to the examples shown in FIG. 2, the hygiene or medical product equipped with chromatography-aided sensors may or may not include a processing unit that can process and transmit the sensor data. If the processor is not included, the sensor data can be read and processed by an external device. If the processor is included, the processed result can be directly displayed to the user via a display mechanism incorporated into the product or can be displayed to the user via an application running on the user's smartphone.

Incorporating the chromatographic properties of the absorbent material into the substance-sensing process can provide a number of advantages. The chromatographic properties are inherent properties of the absorbent material and no additional arrangement other than calibration will be needed. Moreover, compared to the scenario where sensors were embedded or placed non-discriminately, embedding sensors at high-concentration zones increases the sensing resolution. Moreover, by spatially separating the substances, it is also possible to use the same types of sensors (e.g., capacitance or conductance sensors) to detect different products.

Computer System

Figure 12:
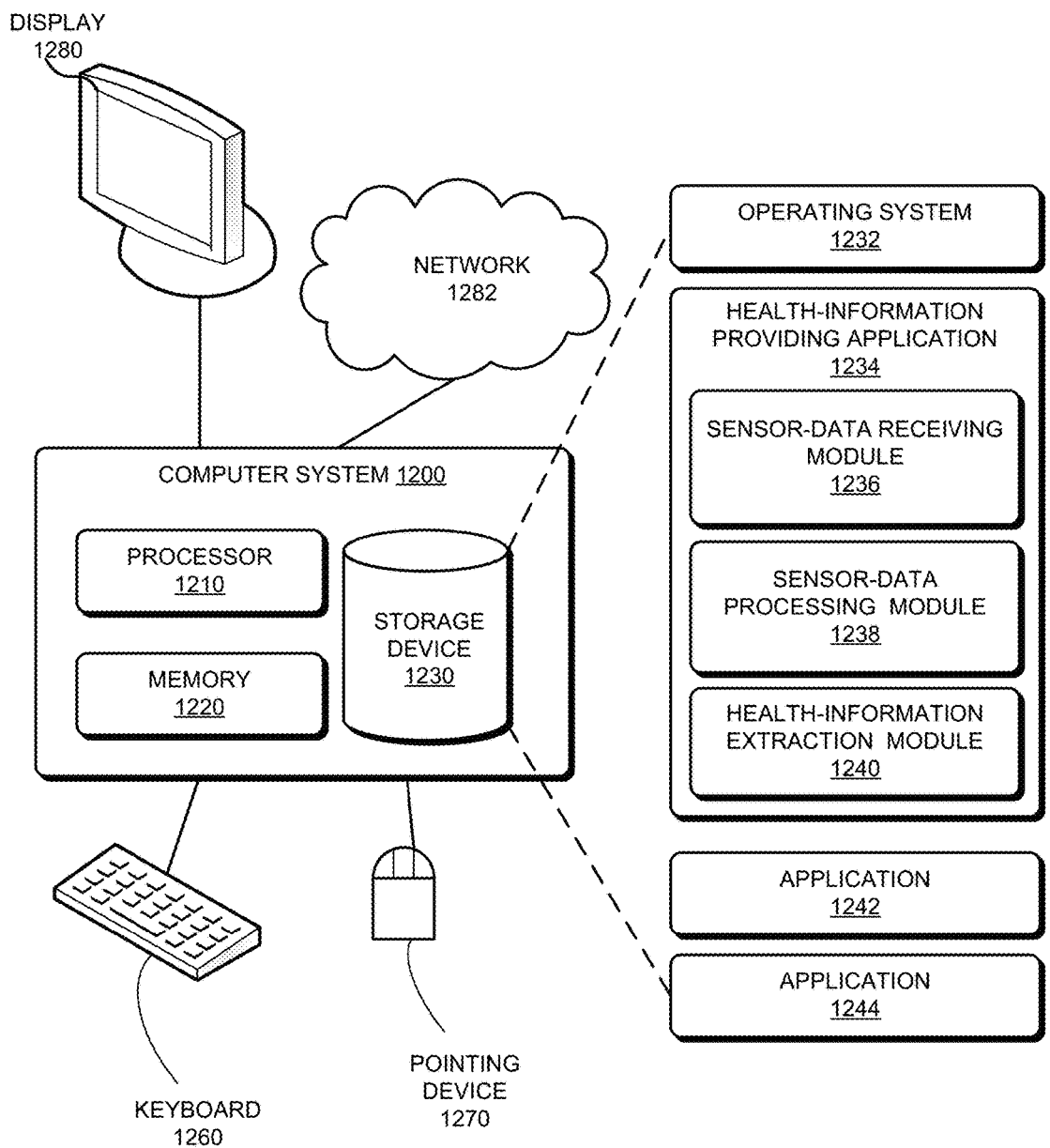
FIG. 12 illustrates an exemplary computer system for providing health-related information, in accordance with an embodiment of the present invention.

FIG. 12 illustrates an exemplary computer system for providing health-related information, in accordance with an embodiment of the present invention. A computer system 1200 comprises a processor 1210, a memory 1220, and a storage 1230. In some embodiments, processor 1210 may include a set of processors. Storage 1230 can store a number of applications, such as applications 1242 and 1244, and operating system 1232. Storage 1230 can also store instructions that can be loaded into memory 1220 and executed by processor 1210 to perform functions that include receiving sensor data, analyzing the received sensor data, and extracting health information based on the analysis. In one embodiment, the instructions in storage 1230 can be part of a health-information providing application 1234 that implements a sensor-data receiving module 1236, a sensor-data processing module 1238, and a health-information extraction module 1240, all of which can be in communication with each other through various means.

In some embodiments, modules 1236, 1238, and 1240 can be partially or entirely implemented in hardware and can be part of processor 1210. Further, in some embodiments, the system may not include a separate processor and memory. Instead, in addition to performing their specific tasks, modules 1236, 1238, and 1240, either separately or in concert, may be part of general- or special-purpose computation engines.

Computer system 1200 can be coupled to an optional display 1280 (which can be a touchscreen display), keyboard 1260, and pointing device 1270, and can also be coupled via one or more network interfaces to network 1282.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, methods and processes described herein can be included in hardware modules or apparatus. These modules or apparatus may include, but are not limited to, an application-specific integrated circuit (ASIC) chip, a field-programmable gate array (FPGA), a dedicated or shared processor that executes a particular software module or a piece of code at a particular time, and/or other programmable-logic devices now known or later developed. When the hardware modules or apparatus are activated, they perform the methods and processes included within them.

The above description is presented to enable any person skilled in the art to make and use the embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present invention is not limited to the embodiments shown, but is to be accorded the widest scope consistent with the principles and features disclosed herein.

What is claimed is:

1. An apparatus for analyzing substances within a liquid, comprising:
    an absorber that comprises one or more layers of absorbent material for absorbing the liquid;
    a flexible substrate comprising one or more sensors embedded within the one or more layers of absorbent material, wherein the sensors are configured to provide information associated with the substances included in the absorbed liquid, and wherein the one or more sensors are arranged in such a way that a location of a respective sensor detecting a respective substance is determined based on a diffusion property of the respective substance; and
    a plurality of printable electrical conductive traces printed onto the flexible substrate, wherein the electrical conductive traces are coupled to the one or more sensors, thereby facilitating transmission of outputs of the sensors.

2. The apparatus of claim 1, wherein the absorber is part of:
    a disposable feminine hygiene product (FHP);
    a disposable diaper; or
    a disposable wound dressing.

3. The apparatus of claim 1, wherein the sensors include one or more of:
    a capacitance sensor;
    a conductance sensor;
    a chemical sensor; and
    a biological sensor.

4. The apparatus of claim 3, wherein the biological sensor includes a printable carbon-nanotube based sensor.

5. The apparatus of claim 1, wherein the liquid comprises body fluid.

6. The apparatus of claim 5, wherein the substances include one or more of:
    a biological substance; and
    a chemical substance.

7. The apparatus of claim 1, further comprising one or more of:
    a microprocessor coupled to the sensors via the electrical conductive traces;
    a near-field communication (NFC) tag; and
    a radio-frequency identification (RFID) tag.

8. An apparatus for analyzing a liquid contained in an absorbent material, comprising:
    a flexible substrate comprising a needle array for penetrating the absorbent material to extract the liquid;
    one or more sensors coupled to the needle array, wherein the sensors are configured to provide information associated with substances included in the liquid, and wherein the one or more sensors are arranged in such a way that a location of a respective sensor detecting a respective substance is determined based on a diffusion property of the respective substance; and
    a plurality of printable electrical conductive traces printed onto the flexible substrate, wherein the electrical conductive traces are coupled to the one or more sensors, thereby facilitating transmission of outputs of the sensors.

9. The apparatus of claim 8, wherein the sensors include one or more of:
    a capacitance sensor;
    a conductance sensor;
    a chemical sensor; and
    a biological sensor.

10. The apparatus of claim 9, wherein the biological sensor includes a printable carbon-nanotube based sensor.

11. The apparatus of claim 8, wherein the liquid comprises body fluid.

12. The apparatus of claim 8, wherein the substances include one or more of:
    a biological substance; and
    a chemical substance.

13. The apparatus of claim 8, further comprising one or more of:
    a microprocessor coupled to the sensors via the electrical conductive traces;
    a near-field communication (NFC) tag; and
    a radio-frequency identification (RFID) tag.

14. The apparatus of claim 8, further comprising:
    a physical enclosure that houses the needle array, the sensors, and the electrical conductive traces; and
    a handle coupled to the physical enclosure to reduce contact between a user of the apparatus and the absorbent material.

15. A feminine hygiene product (FHP), comprising:
    an absorber that comprises one or more layers of absorbent material for absorbing menstrual fluid;
    a flexible substrate comprising one or more sensors embedded within the one or more layers of absorbent material, wherein the sensors are configured to provide information associated with substances included in the menstrual fluid, and wherein the one or more sensors are arranged in such a way that a location of a respective sensor detecting a respective substance is determined based on a diffusion property of the respective substance; and
    a plurality of printable electrical conductive traces printed onto the flexible substrate, wherein the electrical conductive traces are coupled to the one or more sensors, thereby facilitating transmission of outputs of the sensors.

16. The FHP of claim 15, wherein the sensors include one or more of:
    a capacitance sensor;
    a conductance sensor;
    a chemical sensor; and
    a biological sensor.

17. The FHP of claim 16, wherein the biological sensor includes a printable carbon-nanotube based sensor.

18. The FHP of claim 15, wherein the substances include one or more of:
- a biological substance; and
- a chemical substance.

19. The FHP of claim 15, further comprising one or more of:
- a microprocessor coupled to the sensors via the electrical conductive traces;
- a near-field communication (NFC) tag; and
- a radio-frequency identification (RFID) tag.

20. A method for obtaining health information associated with a user of a feminine hygiene product (FHP), the method comprising:
- receiving outputs from one or more sensors embedded in an absorption layer of the FHP, wherein the absorption layer absorbs the user's menstrual fluid, and wherein the one or more sensors are arranged in such a way that a location of a respective sensor detecting a respective substance is determined based on a diffusion property of the respective substance;
- analyzing the outputs of the sensors to obtain information associated with one or more biological or chemical substances included in the menstrual fluid; and
- extracting health information associated with the user based on levels of the biological or chemical substances.

* * * * *